US008684949B2

(12) United States Patent
Hoenes et al.

(10) Patent No.: US 8,684,949 B2
(45) Date of Patent: Apr. 1, 2014

(54) ANALYSIS APPARATUS AND ANALYSIS METHOD FOR BODY FLUIDS

(75) Inventors: Joachim Hoenes, Zwingenberg (DE); Hans List, Hesseneck-Kailbach (DE); Uwe Kraemer, Ilvesheim (DE); Karl Miltner, Frankenthal (DE); Juergen Rasch-Menges, Schwetzingen (DE); Guenther Schmelzeisen-Redeker, Lorsch (DE); Volker Zimmer, Laumersheim (DE); Peter Hess, Mannheim (DE); Paul Jansen, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/333,666

(22) Filed: Jan. 17, 2006

(65) Prior Publication Data
US 2006/0173380 A1 Aug. 3, 2006

Related U.S. Application Data

(63) Continuation of application No. PCT/EP2004/007785, filed on Jul. 14, 2004.

(30) Foreign Application Priority Data

Jul. 16, 2003 (DE) .................................. 103 32 488

(51) Int. Cl.
*A61B 5/00* (2006.01)

(52) U.S. Cl.
USPC ............ 600/583; 600/584; 606/181; 606/182

(58) Field of Classification Search
USPC .......................... 600/573–583; 606/181–182
See application file for complete search history.

(56) References Cited

U.S. PATENT DOCUMENTS

| 4,577,630 | A | * | 3/1986 | Nitzsche et al. | ............... | 606/182 |
| 5,096,828 | A | * | 3/1992 | Ishizaka et al. | .................. | 436/44 |
| 5,686,829 | A | * | 11/1997 | Girault | ............................ | 324/72 |
| 5,741,288 | A | * | 4/1998 | Rife | .............................. | 606/181 |
| 6,036,924 | A |   | 3/2000 | Simons et al. | | |
| 6,306,152 | B1 | * | 10/2001 | Verdonk et al. | ............... | 606/182 |
| 6,589,260 | B1 | * | 7/2003 | Schmelzeisen-Redeker et al. | ............... | 606/181 |
| 6,929,650 | B2 | * | 8/2005 | Fukuzawa et al. | ............ | 606/182 |
| 2002/0052618 | A1 | * | 5/2002 | Haar et al. | ..................... | 606/181 |

(Continued)

FOREIGN PATENT DOCUMENTS

EP 1 238 632 A1 9/2002
EP 1 424 040 A1 6/2004

(Continued)

*Primary Examiner* — Rene Towa
(74) *Attorney, Agent, or Firm* — Bose McKinney & Evans LLP

(57) ABSTRACT

The invention concerns an analytical instrument for assaying body fluids, the instrument having the following features: a) a housing provided with a receiving element for engaging a body part, b) an abutment for the body part which can be moved between a release position and an operating position relative to the receiving element, c) a lancing unit having a lancing element that can pierce the body part resting against the abutment in a linear lancing stroke, d) a test tape unit having a test tape for receiving body fluid issuing from the body part, and e) a detection unit for examining the body fluid applied to a section of the test tape.

49 Claims, 7 Drawing Sheets

(56) References Cited

U.S. PATENT DOCUMENTS

| | | | |
|---|---|---|---|
| 2002/0177761 A1* | 11/2002 | Orloff et al. | 600/309 |
| 2002/0188224 A1* | 12/2002 | Roe et al. | 600/584 |
| 2003/0109777 A1* | 6/2003 | Kloepfer et al. | 600/367 |
| 2003/0144608 A1* | 7/2003 | Kojima et al. | 600/583 |
| 2003/0191415 A1* | 10/2003 | Moerman et al. | 600/584 |
| 2003/0211619 A1* | 11/2003 | Olson et al. | 436/44 |
| 2004/0127818 A1* | 7/2004 | Roe et al. | 600/583 |
| 2004/0225312 A1* | 11/2004 | Orloff et al. | 606/182 |
| 2004/0249406 A1* | 12/2004 | Griffin et al. | 606/182 |
| 2005/0201897 A1 | 9/2005 | Zimmer et al. | |
| 2005/0232815 A1 | 10/2005 | Ruhl et al. | |

FOREIGN PATENT DOCUMENTS

| | | |
|---|---|---|
| JP | 2000-217804 | 8/2000 |
| WO | WO 02/078533 A2 | 10/2002 |
| WO | WO 02/078533 A3 | 10/2002 |
| WO | WO 02/100274 A1 | 12/2002 |

* cited by examiner

ANALYSIS APPARATUS AND ANALYSIS METHOD FOR BODY FLUIDS

REFERENCE TO RELATED APPLICATIONS

The present application is a Continuation of PCT Patent Application No. PCT/EP2004/007785, filed Jul. 14, 2004 which claims priority to German Patent Application No. 103 32 488.7, filed Jul. 16, 2003, which are hereby incorporated by reference in their entirety.

TECHNICAL FIELD

The invention concerns an analyzer for body fluids and in particular a portable blood sugar measuring instrument or device and a corresponding analytical method.

BACKGROUND

Regular blood sugar monitoring is essential for diabetics in order to enable their treatment, diet and rhythm of life to be adjusted to the respective requirements. Handheld instruments operating as mini-laboratories are available on the market for self-monitoring which allow the necessary steps to be carried out simply and rapidly even by laymen. In these instruments disposable test strips provided with a suitable test chemistry are held in readiness to enable a detection inside the instrument for example by an optical measuring unit after being loaded with capillary blood. A lancing device is attached to the instrument to facilitate blood removal which drives out a lancet with an adjustable stroke against a finger placed thereon. However, this requires that the user conveys sufficient blood from the puncture wound onto the test strip without contaminating the instrument as far as possible. The amount of blood that can be obtained at low puncture depths is often inadequate for conventional analytical systems whereas deeper punctures are very painful and lead to scarring of the sensitive finger tips. Another limitation is that the storage of test strips in magazines and their processing requires a large amount of constructed space and complicated drives.

In the EP Application Nos. 02026242.4 and 02028894.0 (corresponding to U.S. Patent Publication Nos. 2005/0201897 A1 and 2005/0232815 A1) which were still unpublished at the time of this application, it is already proposed to use test tapes in the form of cassettes instead of individual test strips in order to apply body fluid to a section of tape that is preferably exposed over a tip and to analyse it. These applications give details about blood collection and the known test media and detection systems in particular for blood glucose to which reference is herewith made and the respective contents are incorporated into this application. However, the previously known systems do not describe the integration of sample collection into a test tape system having an automatic measuring process.

SUMMARY

On this basis the object of the invention is to avoid the disadvantages occurring in the prior art and to improve an instrument or method of the aforementioned type such that a substantially automated measuring process can be achieved with simple handling and optimized collection of the body fluid. In particular it should enable puncturing for blood collection to be achieved with less piercing pain and under hygienic conditions.

The combination of features stated in each of the independent patent claims is proposed to achieve this object. Advantageous embodiments and further developments of the invention are derived from the dependent claims.

Accordingly a test system having the following elements is proposed:

a housing provided with a receiving element for engaging a body part, preferably a fingertip of a test person, an abutment for the body part which can be moved from a release position to an operating position relative to the receiving element, a lancing unit having a lancing element that can pierce the body part resting against the abutment in a linear lancing stroke, a test tape unit having a test tape for receiving body fluids emerging from the body part, and a detecting unit for examining the body fluid applied to a section of the test tape.

The use of a movable abutment in an operating position when the body part rests against it creates in a simple manner a reference position for a defined lancing. This enables a minimum lancing depth to be selected which is still sufficient for the required collection of fluid or blood while reducing the puncturing pain as far as possible. Then a free space for a self-maintained outflow of fluid is created in the release position of the abutment without the abutment becoming contaminated by the fluid or impeding the subsequent collection of the fluid. This allows a spatial and process integration enabling the user a one-step handling in which only one receiving element forms the interface between the instrument and body. The test tape unit enables the hygienic processing of a large number of test elements in the form of tape sections and also simplifies the manufacturing process and handling by the apparatus. It should be noted that although it would be more complicated to control the puncture depth without an abutment, it is basically possible for example by monitoring the lancing force during the lancing process.

The section of test tape that is to be loaded with body fluid can advantageously be transported into the area of the receiving element when the abutment is in the release position so that body fluid can be specifically taken up at the puncture site.

In order to prevent changes in position due to movement by the user it is particularly advantageous when the lancing unit and the test tape unit can be alternately moved into an functional position relative to the receiving element by means of a positioning device.

Another improvement provides that the abutment is formed by a front surface of the lancing unit which faces the receiving element in the operating position. This also minimizes the total distance of the lancing body movement.

According to an advantageous embodiment the lancing unit and the test tape unit can be moved as a common assembly relative to the housing while having a defined position relative to one another. In this connection it is possible that the assembly comprising the lancing unit and test tape unit can be moved linearly in a linear guide. With regard to the utilization of the constructional space it is advantageous when the said assembly can be moved on a curved path which is preferably U-shaped. This can be advantageously achieved by arranging a linkage between the housing and a common support structure for the lancing unit and test tape unit.

Another advantageous embodiment of the invention provides that the lancing unit and test tape unit can be moved alternately into the area of the receiving element on separate paths by means of specially dedicated delivery means that are preferably coupled to one another. In this connection the delivery means are advantageously formed by a rack-and-pinion drive or rotary lever drive.

It is also advantageous when the abutment is formed by a movable tape guide for the test tape. In this manner the moved masses can be kept low and the space required is further reduced. The abutment can advantageously be moved to a limited extent in the lancing direction by means of a curve control device which is typically a switchable cam disk. The structure of the instrument can be further optimized due to the fact that the tape guide distally spans the lancing unit preferably in an arched manner towards the receiving element.

In order to make allowance for the restricted space, it is advantageous when the test tape unit has a reciprocating deflecting head to form a tape loop in the area of the receiving unit. Another improvement provides that the deflecting head is tapered in a convex or angled manner towards the receiving unit.

It is advantageous for a compact design and defined measuring conditions when the detection unit which preferably employs reflection photometry is located in the deflecting head.

The lancing process can be optimized by the fact that the abutment in the operating position forms a reference means for determining the magnitude of the lancing stroke. Another improvement provides that the abutment and/or the test tape are provided with a piercing opening for the lancing body.

The lancing unit advantageously has an adjusting device which can be preferably operated from outside the housing for adjusting the lancing stroke relative to the abutment. It is also advantageous when the lancing unit has a trigger preferably arranged on the outside of the housing for manually actuating the lancing stroke.

A preferred embodiment provides that the test tape unit is formed by a tape cassette for transporting the test tape in sections preferably by means of winding spools. The tape cassette preserves the integrity of the tape store and the test elements in the form of tape sections can be processed by the instrument in a technically simple and hygienic manner.

A plurality of lancets can be advantageously stored as a lancing element in a preferably exchangeable lancet magazine. The test tape can have at least 15 and preferably more than 50 sections of test tape that can be positioned relative to the receiving unit by advancing the tape for successive examinations of body fluid. In this connection it is advantageous when the ratio of stored lancing elements to test tape sections is between 1:1 and 1:50.

Another advantageous embodiment provides that the receiving element has a compression element for increasing the internal pressure of the body fluid in the pressed body part in order to thus obtain sufficient fluid even with a low puncture depth. In this connection it is advantageous when the compression element is formed by a preferably conical press ring for bulging the body part against the lancing element.

In a particularly simple embodiment it is provided that a section of the test tape that is clamped in the area of the receiving element acts as an abutment to form a reference position for the lancing stroke.

Whereas the abutment can be moved backwards and forwards between the release and operating position, a possible kinematic reversal provides that the abutment can be moved into the release and operating position relative to the receiving element by a displacement or compression movement of the receiving element.

In order to monitor the dose of the applied body fluid it is advantageous when the detection unit has several measuring points located next to one another on a section of the test tape.

In order to achieve an automatic blood application even when the space in the instrument is confined, a tape deflecting unit is advantageous which allows a loop of the test tape to be pulled out away from the tape guide in the area of the receiving element. For this purpose it is advantageous when the tape deflecting unit is a deflecting roller which guides the test tape and can move backwards and forwards or a spring elastic deflecting tongue which guides the test tape.

A simple constructional embodiment provides that the tape deflecting unit has a drive which is capable of reciprocating movement and preferably a pivoting lever drive for a backwards and forwards movement to pull out and retract the tape loop.

According to another aspect of the invention it is proposed that at least two of the instrument components can be moved alternately into their respective operating positions relative to the receiving element where the instrument components are preferably arranged on a common support structure and the support structure can be moved in order to position the instrument components into their respective operating position relative to the housing. This allows complex processes to be completely integrated even in the small amount of constructional space that is available in a handheld instrument.

In this connection it is advantageous when
    the support structure can be moved into the respective end position of the instrument components by means of a positioning device and preferably on a curved path;
    the support structure consists of a platform provided with attachment elements for the instrument components;
    the support structure has clamping, screwing or locking members to locate the instrument components preferably in a detachable manner;
    the support structure has attachment points for the instrument components that are preferably arranged in a grid shape;
    the unit for the test means has a magazine for processing and in particular for the provision and disposal of a plurality of test strips.

The following steps are proposed to achieve the aforementioned object with regard to a process:
    a body part, preferably a finger pad of a test person is engaged with a receiving element of an instrument housing whereby an abutment is contacted by the body part,
    a lancing member is lanced in a linear lancing stroke into the body part resting against the abutment,
    afterwards when the lancing member is retracted, the abutment is moved into a release position and
    body fluid escaping from the body part is applied to a section of a test tape that is moved into the area of the receiving element and analyzed by a detection unit.

These and other features and advantages of the present invention will be more fully understood from the following detailed description of the invention taken together with the accompanying claims. It is noted that the scope of the claims is definitely by the recitations therein and not by the specific discussion of the features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Figure 1:
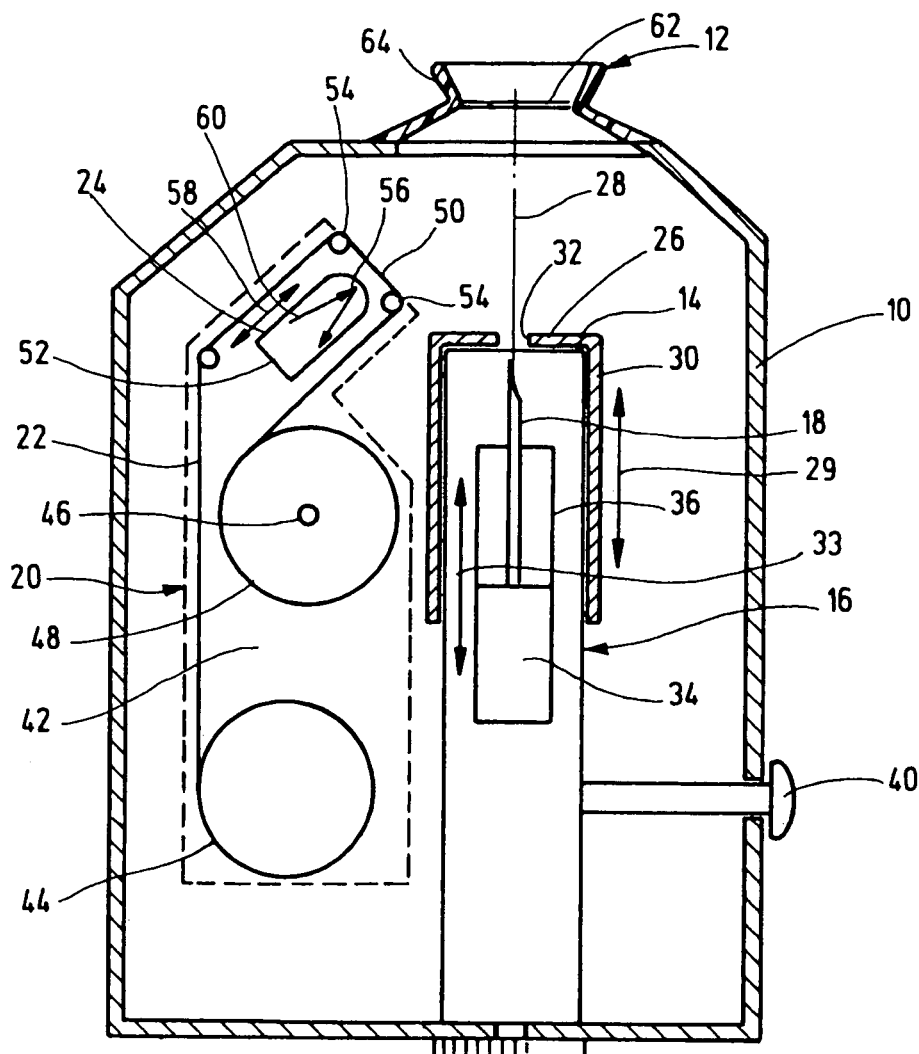
FIG. 1 shows a portable blood sugar measuring instrument for diabetics with a lancing and test tape unit in a sectional view.

Skilled artisans appreciate that elements in the figures are illustrated for simplicity and clarity and have not necessarily been drawn to scale. For example, the dimensions of some of the elements in the drawing figures may be exaggerated relative to other elements to help improve understanding of the embodiment(s) of the present invention.

In order that the invention may be more readily understood, reference is made to the following examples, which are intended to illustrate the invention, but not limit the scope thereof.

DETAILED DESCRIPTION

The following description of the preferred embodiments is merely exemplary in nature and is in no way intended to limit the invention or its application or uses.

The blood sugar measuring instrument shown in FIG. 1 comprises a housing 10, a blood collection cone 12 attached thereto as a receiving element for a finger of a test person, an abutment 14 inside the housing which interacts with the blood collection cone 12, a lancing unit 16 with a lancing member 18 for piercing the finger, a tape unit 20 containing a test tape 22 for applying the blood emerging from the finger puncture and a detection unit for examining the blood on the test tape 22.

The abutment 14 can be moved between a release position and an operating position relative to the blood collection cone 12. In the operating position it is possible by contacting the body part to be punctured, to determine a reference position for a defined puncture depth whereas in the release position the blood can emerge unhindered from the generated skin opening and a free space is created for receiving a drop of blood on the test tape 22. Thus the lancing process and the blood application take place at the same site in the area of the blood collection cone 12 so that the user does not have to carry out a movement to change the position and the measurement process can be carried out completely automatically.

In the embodiment shown in FIG. 1 the abutment 14 is formed by a front surface 26 facing towards the blood collection cone 12 of a front cap 30 of the lancing unit 16 which can be moved in the lancing axis 28 in the direction of the double arrow 29. The front surface 26 is provided with a piercing opening 32 through which the lancing member 18 can pierce in a linear lancing stroke (double arrow 33). For this purpose the lancing unit 16 has a lancing drive 34 which can be coupled to a lancing member 18 formed by a lancet. In this connection it is envisaged that a plurality of lancets 18 can be stored in a magazine 36. In order to adjust the lancing stroke relative to the abutment 14, the lancing unit 16 has an adjustment device 38 that can be operated from outside of the housing. As a further external operating element the lancing unit 16 has a trigger 40 which allows a manual triggering of the lancing stroke of the lancing drive 34 by the user.

The tape unit 20 comprises a cassette 43 in which the test tape 22 can be pulled from a supply spool 44 and reeled onto a take-up spool 48 by means of a tape advance drive 46. The test tape 22 has a plurality of tape sections 50 which are coated with dry chemicals that react with the blood fluid that is applied thereto resulting in an optically detectable color change that corresponds to the blood sugar concentration.

A deflecting head 52 is provided to form a tape loop that can be positioned in the area of the blood collection cone 12. The said deflecting head with its convex guide surface 56 can be moved in the direction of a double arrow 58 backwards and forwards relative to the exposed section of tape 50 between deflecting rollers 54 so that a drop of blood can be taken up onto the tape section 50 in the area of the blood collection cone 12 even when the constructional space is confined. The deflecting head 52 is also equipped as a detection unit 24 with a reflection photometric measuring device 60 in order to carry out an optical detection measurement on the section of tape 50 that is loaded with blood.

The blood collection cone 12 increases the internal pressure in the pressed body part. This allows sufficient amounts of capillary blood to be already obtained with very small puncture depths and correspondingly less puncture pain. A ring lip 64 with a double conical taper towards an engagement opening 62 that is made of an elastomeric material is provided for adaptation to different finger contours. This results in a ring-shaped lateral compression when it is pressure deformed by an engaging finger which results in a bulging of the finger tip towards the abutment 14 and towards the lancing member 18. Such a finger cone is known from German patent application DE-A 100 26 172 for forming a dammed-up volume of blood in the finger tip in combination with a test strip system. In general receiving elements adapted to the anatomy of other parts of the body are also conceivable instead of the ring lip 64. Thus it is for example possible to form the housing 10 or the engagement opening 62 over a large rigid cone which can be placed on the lower arm. The palm of the hand or earlobe can also be used as further alternative puncture sites. However, in general it is easiest to collect blood from the finger pad although a high concentration of nerve ends at this site makes the puncture relatively more painful.

Figure 2:
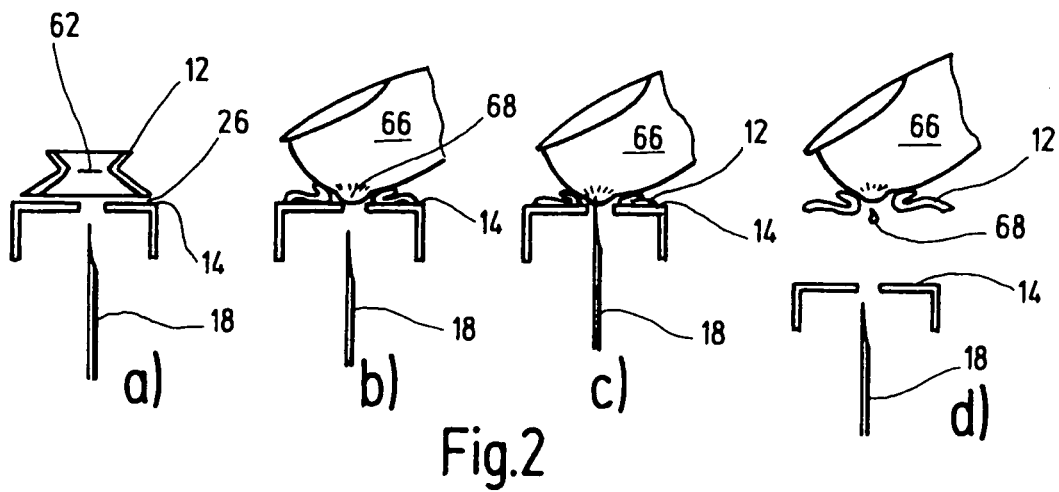
FIG. 2a to d show various steps for collecting blood at a blood collection cone of the blood sugar measuring instrument according to FIG. 1 in a partial enlargement.

The process of blood collection takes place as illustrated in FIG. 2. FIG. 2a shows the abutment 14 in an operating position relative to the blood collection cone 12 where the end face 26 of the engagement opening 62 faces the inner side of the housing. According to FIG. 2b the user presses a finger 66 against the elastically deformable blood collection cone 12 until the finger pad 68 makes contact with the end face 26. The lancet 18 is then advanced and retracted by an exactly adjustable stroke travel through the piercing opening 32 to beyond the end face 26 (FIG. 2*c*). The abutment 14 together with the lancet 18 is then withdrawn away from the blood collection cone 12 into the release position in order to create a free space for blood to escape. While the user still keeps his finger 66 pressed on, a drop of blood 68 which has emerged can be applied to the loop-shaped exposed section of tape 50 by an advancing motion of the deflecting head 52. Afterwards the user can lift his finger 66 from the blood collection cone 12. After the detection measurement has been carried out by the measuring device 60, the result is displayed on a display that is not shown. Finally the used section of tape 50 is reeled on so that the instrument is again ready for measurement.

Figure 3A:
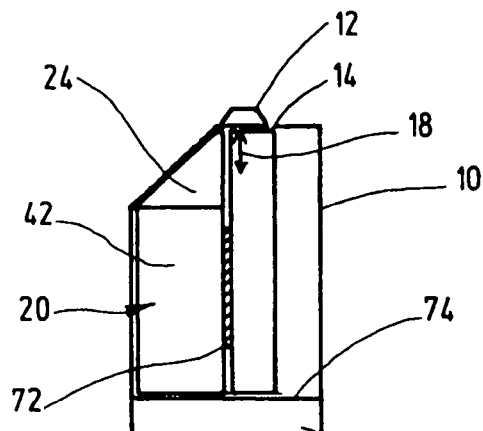
FIGS. 3a and b show an embodiment of a blood sugar measuring instrument with a lancing and tape unit assembly that can be moved linearly.
Figure 3B:
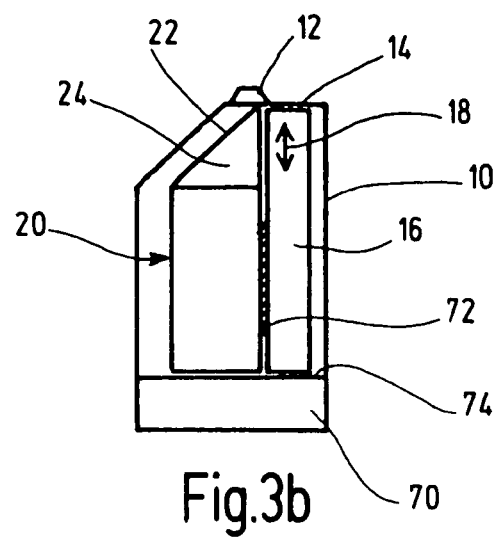

In the embodiments shown in the following drawing figures, identical or similar components are labelled with the same reference numerals as described above. According to FIG. 3 the lancing unit 16 and the tape unit 20 (tape cassette 42) can be alternately brought into an operating position relative to the blood collection cone 12 by means of a positioning device 70. For this purpose the units 16 and 20 can be moved in a fixed position 72 relative to one another as an assembly in a straight line in a linear guide 74 by means of a rigid support structure 72. In the displacement position according to FIG. 3*a* it is possible to actuate the lancing member 18 whereas in the position shown in FIG. 3*b* the test tape 22 can be activated for blood application by means of the deflecting or measuring head 24 that tapers at an acute angle.

Figure 4A:
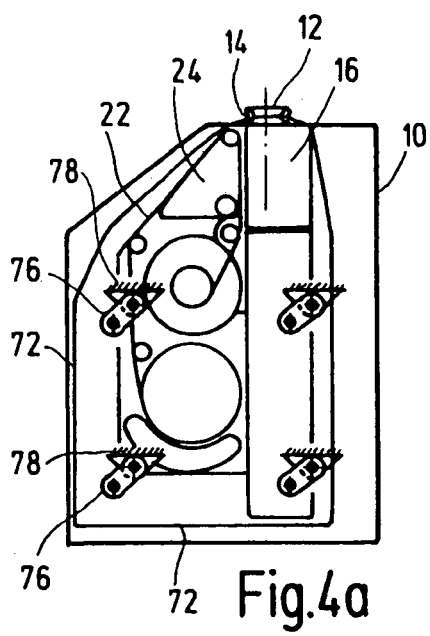
FIG. 4a to c show another embodiment with a swivel-mounted lancing and tape unit assembly.
Figure 4B:
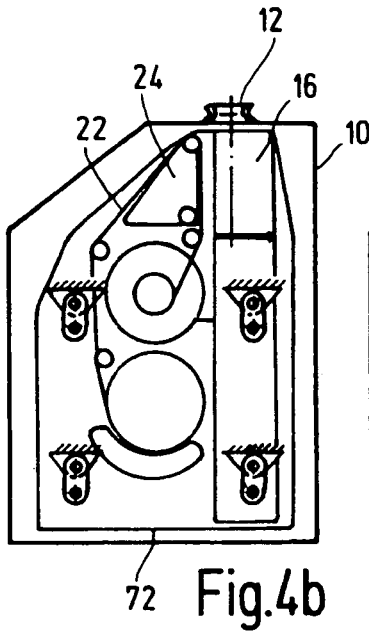
Figure 4C:
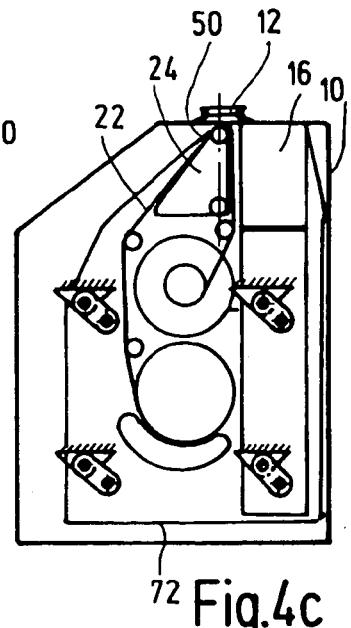

In the embodiment shown in FIG. 4, the support structure 72 for the lancing and tape unit is guided on a U-shaped path curve. The support structure 72 is connected via four pivot arms 76 with rigid hinged joints on the housing. In the pivot position according to FIG. 4*a* the lancing unit 16 is positioned opposite to the blood collection cone 12. In the middle pivot position according to FIG. 4*b*, the blood collection cone 12 is released for blood to escape. The tape unit 20 is positioned in the pivot position according to FIG. 4*c* in which a loop-shaped section of tape 50 engages in the area of the blood collection cone 12.

Figure 5A:
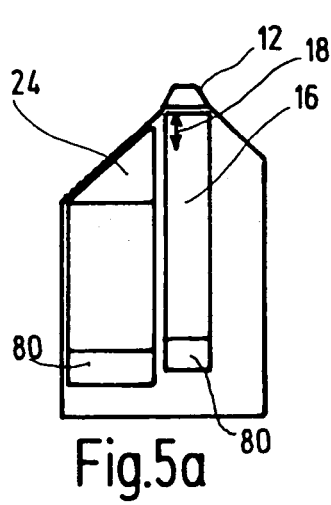
FIGS. 5a and b show another embodiment with a lancing unit and tape unit which each can be moved separately.
Figure 5B:
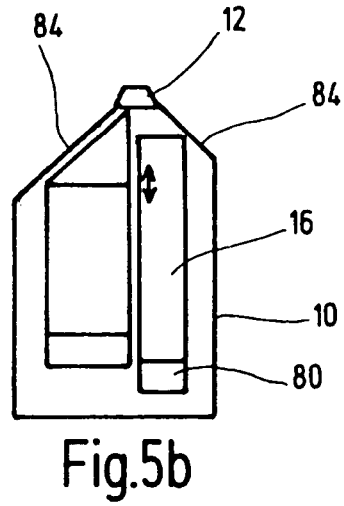
Figure 6:
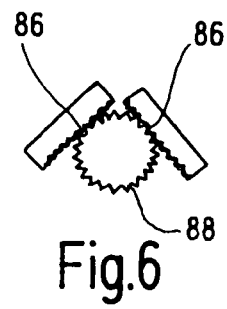
FIG. 6 shows a rack-and-pinion drive for alternately moving the lancing unit and tape unit in a coupled manner.

In addition to the described linear or U displacement it is also conceivable to have other curve-shaped movement paths in order to achieve an advantageous positioning with regard to a compact instrument design. For this purpose separate delivery means 80, 82 are provided according to FIG. 5 with which the lancing unit 16 and the tape unit 20 can be alternately moved on separate paths into the area of the blood collection cone 12. The asymmetric design of the detection unit 24 and the asymmetric lancing position of the lancing unit 16 relative to the central axis of the blood collection cone 12 enables the displacement movements to be minimized. In addition the housing 10 can also be given a compact design by walls 84 which taper towards the blood collection cone 12. In order to couple the delivery means 80, 82 they can consist of gear racks 86 according to FIG. 6 which can be alternately moved towards the blood collection cone 12 by means of a common gear wheel 88.

Figure 7:
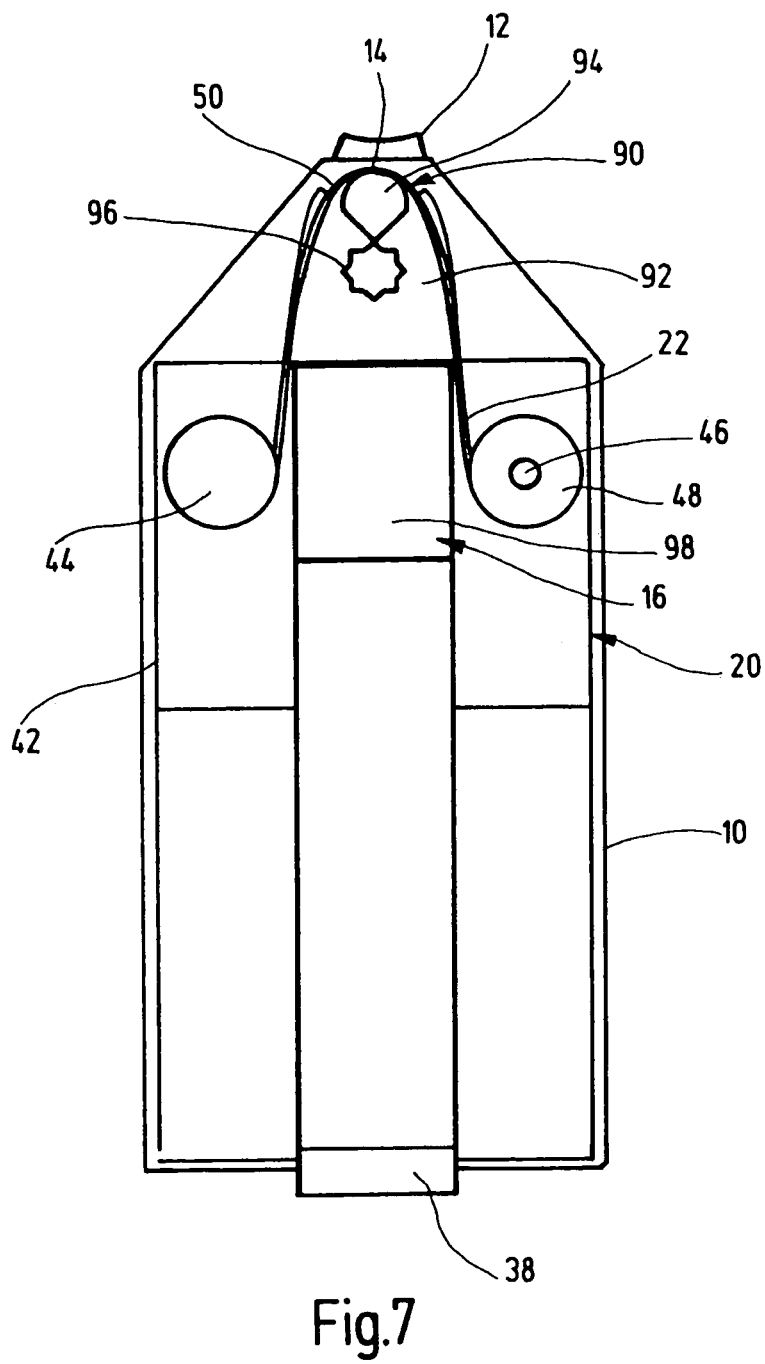
FIG. 7 shows an embodiment of a blood sugar measuring instrument in cross-section with a tape guide that can be moved backwards and forwards.
Figure 8:
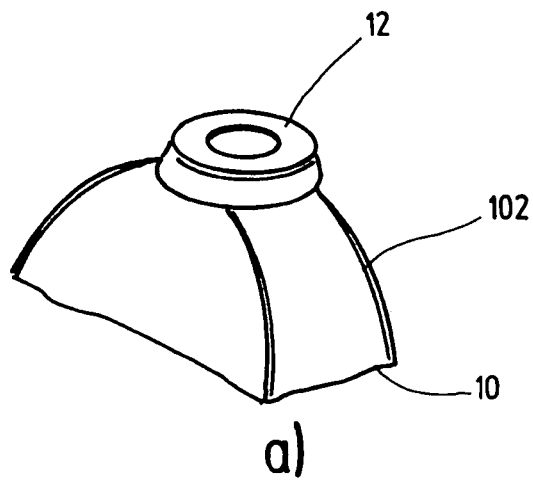
FIG. 8a to c show a tape guide that can be moved between an instrument housing and an inner shell in a partial perspective diagram.
Figure 8:
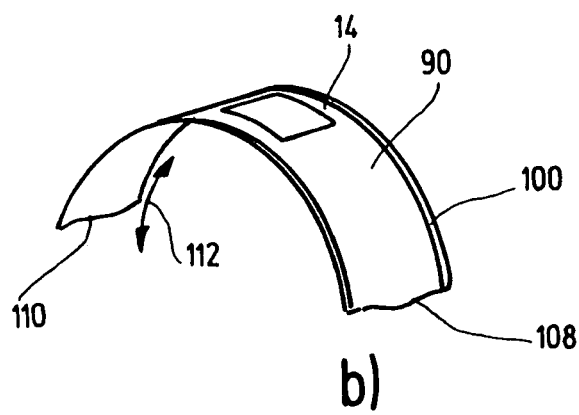
Figure 8:
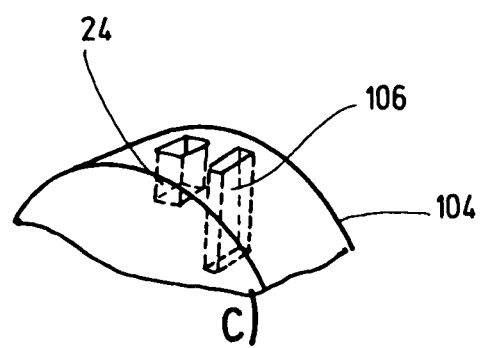

In the embodiment shown in FIGS. 7 and 8 the lancing unit 16 and the tape unit 20 are rigidly arranged in the instrument whereas the abutment 14 is formed by a movable tape guide 90 for the test tape 22 whose movement is limited in the lancing direction. The tape guide 90 has a support element 94 supported in the head piece 92 of the lancing unit 16 which can be displaced towards and away from the blood collection cone 12 by turning a cam disk 96.

In the initial state before the lancing movement, the supporting element 94 is in the upper position on a cam of the cam disk 96 shown in FIG. 7. The user compresses the blood collection cone 12 slightly until his finger touches the abutment 14. After triggering the lancing one of the lancets that is kept ready in a drum magazine 98 is moved to and fro through the tape loop 50 which is further elucidated in the following on the basis of FIG. 9. In order not to hinder the escape of blood, the support element 94 is subsequently lowered slightly by rotating the cam disk 96 into an intermediate position between the cams. During a specified waiting time a tape section 50 to be loaded is positioned on the support element 94 by the feed drive 46 and kept in abutment. The cam disk 96 is then rotated further until the support element 94 again rests on a cam and the lifted section of tape 50 collects the drop of blood on the finger.

A shell-shaped guide frame 100 can also be used as a tape guide 90 (FIG. 8*b*) which is arranged between an outer housing shell 102 (FIG. 8*a*) and an inner housing shell 104 (FIG. 8*c*) and has a limited amount of movement in the lancing direction. In this case the outer shell 102 carries the blood collection cone 12, and a guide shaft 106 for the lancets and an optical detection unit 24 are attached to the inner shell 104. In this arrangement it is possible that the guide frame 100 that arches in a curved manner towards the blood collection cone 12 is only movable at one end 110 by a predetermined swinging stroke whereas the other end of the frame 108 is located in a fixed position on the tape cassette 42.

Figure 9A:
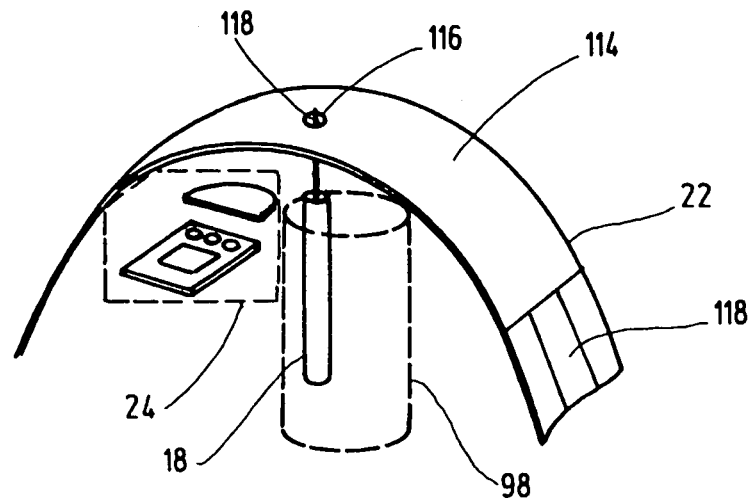
FIGS. 9a and b show an illustrative diagram of the lancing action through the test tape and the subsequent optical detection.
Figure 9B:
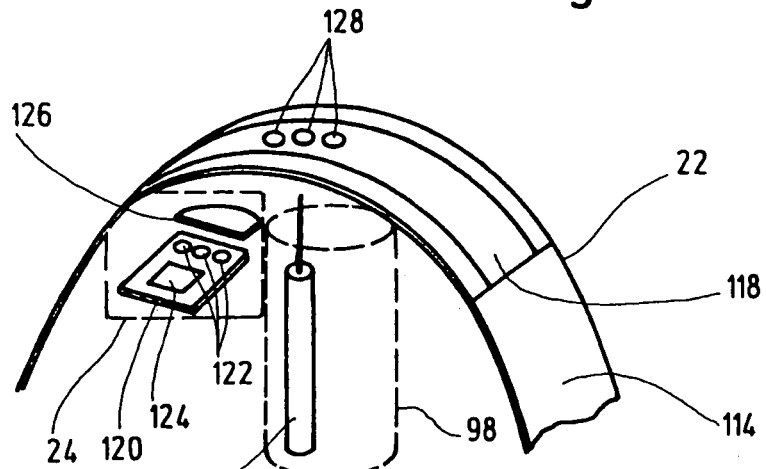

As shown in FIG. 9*a* the lancing process can take place directly through a thin support foil 114 of the test tape 22 where it is expedient that a pilot hole 116 positioned in the lancing axis prevents unintentional damage to the lancet tip 118. Sections of the support foil 114 are coated with a test field 118 which, after the lancing process, is advanced with the tape into the blood collection and measuring position shown in FIG. 9*b* by suitable control devices such as a light barrier or a mechanical aperture mask guide. The optical detection unit 24 used for a contactless detection comprises a measuring circuit board 120 with three light sources (LEDs 122) and a photosensor 124 as well as collection optics (lens 126). The LEDs 122 are arranged in a row and correspondingly generate a row of three light spots 128 in the direction of tape transport by means of the lens 126. The said light spots are located on the test field 118 in the area of the lancing axis above the transparent support foil 114. In order to unequivocally assign the light reflected from the light spots 128 using only one sensor 124, the LEDs 122 are actuated successively. In this arrangement the middle LED is used for the actual detection measurement whereas the two outer LEDs enable a control of the dosage. An erroneous dosing is detected when there is an asymmetric signal distribution. The test field 118 contains dry chemicals that respond to the analyte (glucose) in the applied blood fluid and result in a change in the reflected light radiation.

Figure 10:
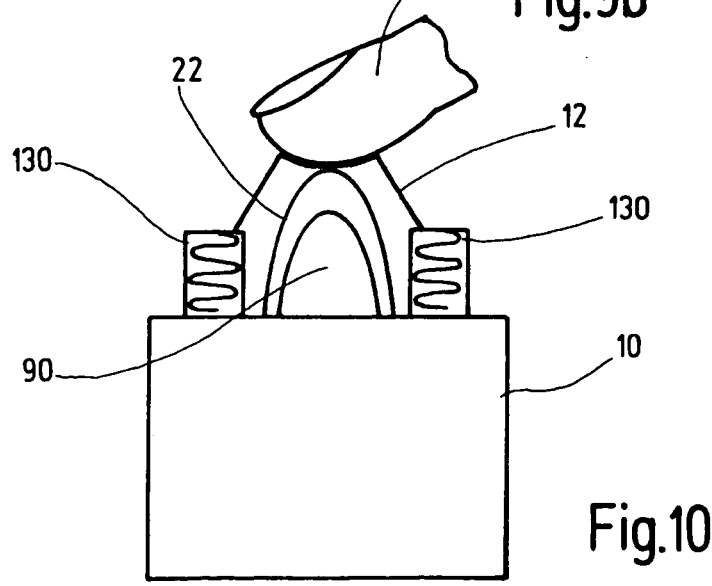
FIG. 10 shows a spring-mounted finger cone in a very simplified section.

The greatly simplified drawing in FIG. 10 shows a blood collection cone 12 which is supported by spring elements 130 relative to the housing 10 in such a manner that a movement is possible relative to the test tape 22 or its guide 90 under the pressure of the finger 66. The spring elements 130 can be designed to be similar to a corrugated bellows and should become harder in a non-linear manner with increasing deformation. In this connection it is also conceivable that the abutment 14 is formed by the stretched support foil 114 and can be brought into the operating or release position relative to the receiving element by a backwards and forwards movement of the blood collection cone 12.

Figure 11:
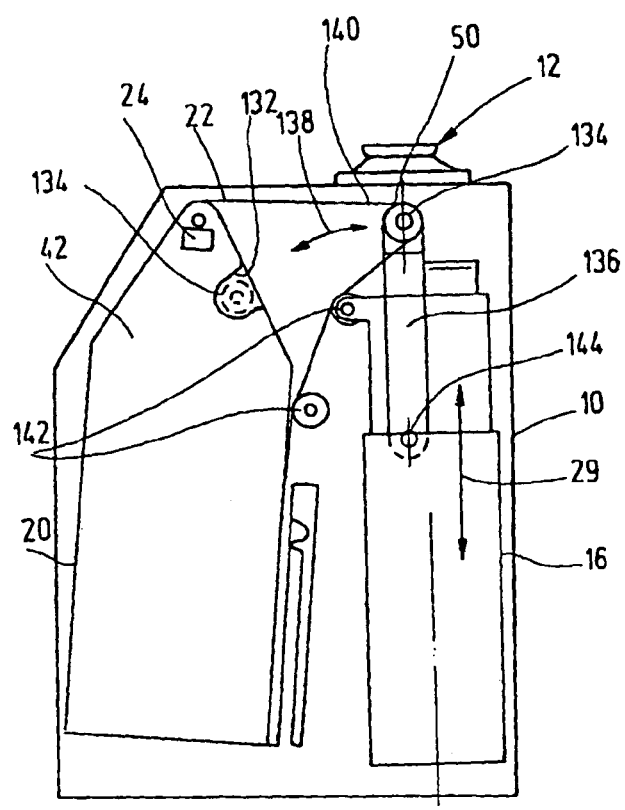
FIGS. 11 and 12 show other embodiments with a pivoted lever mechanism to draw out a tape loop from a cassette in two different views.
Figure 12:
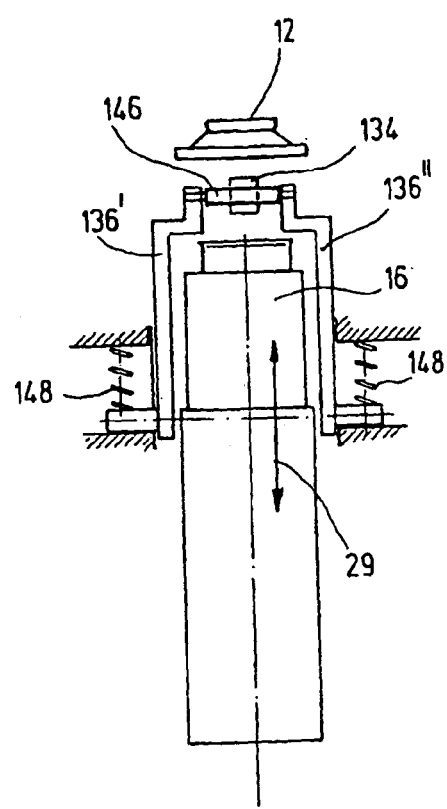

In the embodiment shown in FIGS. 11 and 12 the tape cassette 42 has a clearance 132 at a suitable position in which a deflecting roller 134 engages when the cassette is inserted. This roller 134 is supported at the free end of a pivoted lever 136 which can execute a reciprocating swivel movement in the direction of the arrow 138. If, after the skin has been punctured, the lancing unit 16 or at least the front part thereof is moved back (arrow 29), the roller 134 can swing out and thus pull a tape loop 140 out of the cassette 42 and move it to the site of blood collection. The distance over which the lancing device has to be moved is essentially defined by the diameter of the roller 134 which can be relatively small (e.g. 3 mm). Two additional guide rollers 142 are provided to prevent the test tape 22 from exerting adverse forces for example on a seal of the cassette 42 during this movement and, on the other hand, to prevent it rubbing against other instrument structures.

As it swings out the lever 136 with the roller 134 pulls out fresh tape 22 from the supply spool which is not driven but only braked. This ensures that after the swivel movement a test field 50 provided with detection chemicals lies under the cone 12. On its swivel movement the roller 134 is specifically guided in a curve from below to the punctured skin so that it (viewed from the cassette 42) arrives at the finger across from the puncture site. As a result the tape loop 140 is not only quasi rolled out onto the skin but is gently moved from below to the site where blood escapes. This is carried out by the motor force of a pivot drive 144.

When this position is reached, the lever 136 is uncoupled from the motor drive and it continues to stand towards the outside under weak spring tension. This keeps the tape 33 under tension. Such a drive which can automatically uncouple can readily be achieved with a cam.

Afterwards the tape 22 is reeled in from the take-up roller to such an extent that the site wetted with blood comes to rest in front of the detection unit 24. With a suitable arrangement of cone 12, cassette 42 and pivot point of the lever 136, the tape 22 nestles at this moment over the tip of the cassette which positions it precisely in front of the optics of the detection unit 24. During this phase in the sequence the roller 134 is hauled in on its lever 136 which is now only spring-loaded like a pulley. The spring loading in this case ensures that the tape never becomes slack. A special advantage is that a clean tape movement occurs without contaminating instrument structures with blood even in those cases in which the body part to be lanced cannot be exposed very far into the instrument.

A preferred embodiment according to FIG. 12 consists in the fact that the roller 134 is clipped into the recess 132 of the cassette 42. When the cassette 42 is inserted, the roller is automatically attached to the bearing pin 146 on the lever arm 136' without the user having to take care of it. At the end of the movement cycle the roller is again clipped by a motor drive into the arrestment so that when the cassette 42 is removed from the housing 10, it can be hygienically disposed as a component of the cassette.

In order that the roller 134 cannot become detached from the pin 146 by the force of gravity or knocks, it has to be guided axially. This can be achieved by guide ribs (not shown) that run along the path of movement of the roller 134 which restrict the freedom of movement in the axial direction and optionally additionally act as an auxiliary guide for the tape. Alternatively the lever 136 is in two parts (136' and 136"). One lever arm 136' with the bearing pin 146 is driven in a pivoted manner whereas the second lever arm 136" is pressed towards the cassette under a slight spring load but is stopped there at a solid stop. If the first lever 136' with the roller 134 now pivots away from the cassette 42, it takes along the second lever 136" with the protruding end of the bearing pin 146 which thus provides an axial stop for the roller 134.

The two levers 136', 136" are pivoted on both sides of the lancing unit 16 and the bearings are in alignment. A special embodiment allows a movement of the bearing axes towards the finger cone 12 against the restoring force of the springs 148. When the double lever has swung out the tape into the pick-up position, the roller 134 is exactly under the cone 12 but does not yet touch the finger pad. The test field on the test tape 22 wraps around at least the upper hemisphere of the roller 134. Once this state has been reached, the lancing unit 16 moves upwards and in doing so buts against the spring-mounted double lever 136 whereupon it is taken along by it. As a result the roller 134 with the test field that is wrapped around it dabs into the drop of blood that has escaped. Subsequently the lancing unit 16 moves back during which the springs 148 retract, the lever 136 and thus the roller 134 away again from the finger.

Another embodiment that is not shown uses a simple tongue made of metal sheet instead of a roller 134 which draws out the tape 22 in its (rigid) longitudinal direction but bears it resiliently against the skin in its transverse direction in which it is flexible. It is also conceivable that the cassette 42, the detection unit 24 and the lancing unit 136 do not lie in one plane. The flexibility of the tape 22 would then allow it to move towards a lancing site at an angle to the cassette plane with a lateral excursion at right angles to the tape loop.

In the case of a very rapid chemical reaction on the test element it may be necessary to use the measuring device to already monitor the application of blood. For this purpose a loop of tape can be transported to the site of blood application by a detection unit designed as a deflecting head 56 as described above for FIG. 1. In this connection it is advantageous to clamp the tape loop on the deflecting head and to move it to the sample in this immobilized state. This clamping can be achieved by means of a fork which is arranged in the traverse path of the deflecting head and is taken along to the site of blood application by the deflecting head against a spring load. In this process the deflecting head engages between the arms of the fork such that the test tape is firmly and immovably clamped.

The pulling out of a tape loop can also be used to advantage when not only the test tape together with the detection unit are transported to the site of blood application but also when additionally the lancing unit is moved with them in close proximity. In this case the lancing occurs through a section of support tape located between the test fields. After retraction to allow blood to discharge, the next test field behind the wound is spooled, the blood is taken up by a forwards movement and after another retraction the test field is spooled over the detection unit. Also in this case a separate lateral movement of a section of tape in the form of a tape loop is helpful in addition to the mere rewinding of the tape from the supply spool to the take-up spool.

Figure 13:
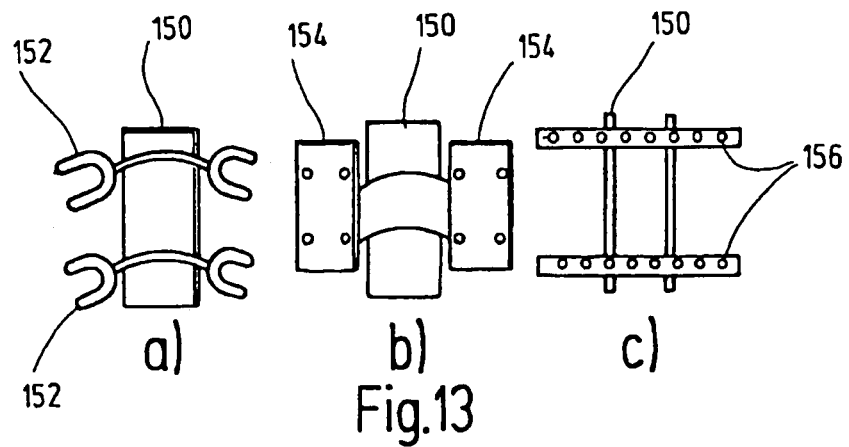
FIGS. 13a, b, c show embodiments of a platform for attaching several instrument components.
Figure 14:
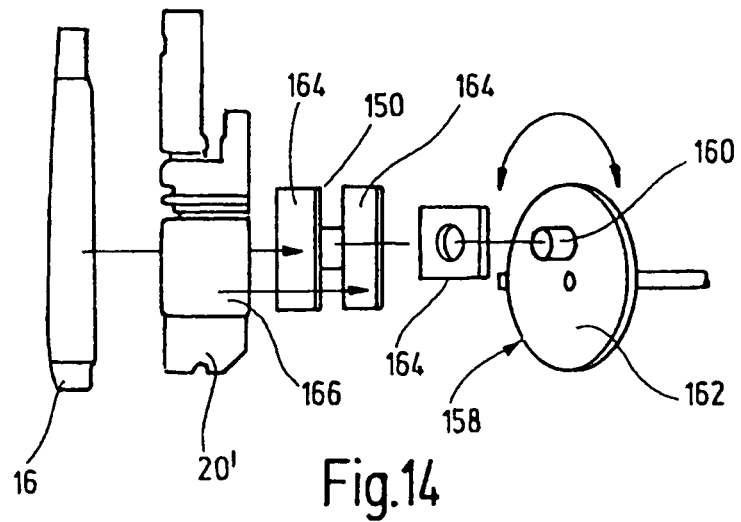
FIG. 14 shows two instrument components for fitting onto a platform in conjunction with a positioning drive in a simplified illustrative view.
Figure 15:
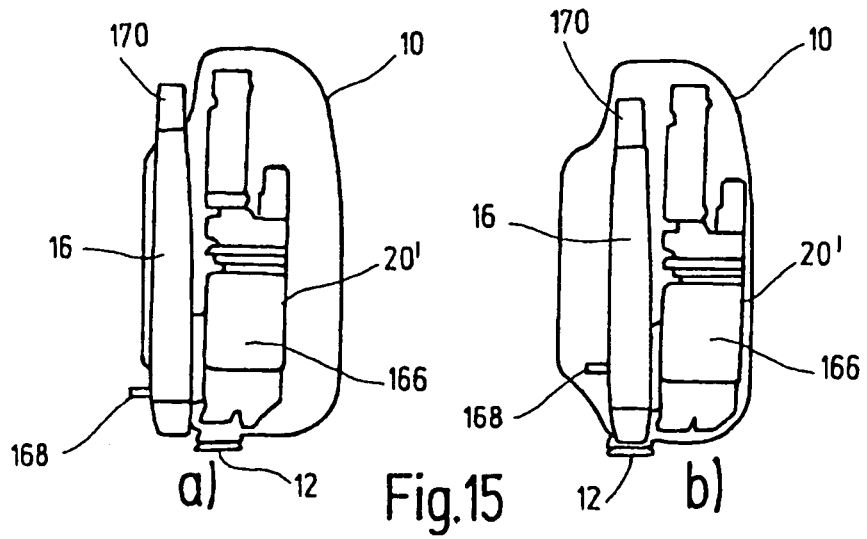
FIGS. 15a, b show the embodiment according to FIG. 14 in an instrument housing in two different operating positions.

In the embodiment shown in FIGS. 13 to 15 a movable platform 150 is envisaged as a core piece on which the instrument components required to carry out blood collection and analysis or other instrument functions can be attached. Any possible embodiment of a support structure for components that are to be attached thereto can come into consideration as a platform. For example FIG. 13a illustrates a platform 150 with clamping devices 152 mounted thereon whereas FIG. 13b shows a base 150 with assembly plates 154 mounted thereon and FIG. 13c shows a base 150 in the form of a grid construction with variable attachment points 156.

The platform 150 is movable within the housing 10 in order to position the components attached thereto for obtaining blood, blood collection or other functions. The target position is defined in particular with reference to the finger receiving element 12 of the housing 10. In this connection the platform 150 should if possible be moved such that the components attached thereto can be moved to their corresponding target positions in a distal direction. An arc-shaped (semi circular) movement is preferably selected for this. If there are more than two components, the arc-shaped movement can be executed successively for a corresponding number of times. In this connection the width of the arc of the individual movements can also be adapted to the required dimensions of the components that are used i.e. arcs of different width are executed.

The movable platform 150 can either be adjusted as a unit or the individual attachment points of the attached components can be adjusted. The direction of movement of the adjustment motion preferably runs axially to the receiving element 12 so that the height of all the units or of the individual components can be adjusted. The adjustment is either carried out manually e.g. during assembly or automatically during the measurement operation. An individual adaptation to the respective user is also conceivable.

As illustrated in FIG. 14, a simple electromechanical positioning device 158 can move the platform 150 to position the lancing unit and test means unit 20' attached thereto. In this case the movement occurs by rotating a pin 160 on disk 162 in a slotted link 164. It is for example also possible to transfer the movement by translating the rotational movement of a lever or directly by rotating a gear wheel in a slotted link on the movable platform 150 (not shown). In this connection it is important that the respective end positions are stable.

Attachment areas 164 for the components 16, 20' to be moved are provided on the movable platform 150. It is obvious that any suitable attachment elements meeting the requirements of the respective instrument components can be used and do not therefore have to be described in more detail. What is specially shown is the modular platform combination of individual components 16, 20' which are already well-known and commercialized under the trademark Accu-Chek® Compact blood glucose monitoring system. The lancing aid 16 enables a lancing movement of a lancet to be triggered while the module 20' comprises a drum magazine 166 with an output and push rod for automatic blood collection onto individual test strips and measuring optics as a detection unit for blood glucose analysis.

FIG. 15 shows the assembled instrument. In the example shown the end of the lancing aid 16 protrudes from the housing (FIG. 15a). Thus the button 168 can still be operated by the user to tension the lancing aid and lancets can be changed as usual when required by removing the lower cap 170. After the start of the measurement the wheel 162 located behind the movable platform 150 rotates and moves the lancing aid 16 in an arc shape by means of the pin 160 and the slotted link 164 into the lancing position above the receiving member 12 (FIG. 15b). Then the lancing operation can be triggered either manually by the user or by an automated function.

After the lancing operation is completed the movable platform 150 with the components 16, 20' attached thereto can be moved back into the initial position by rotating the positioning device 158 in the opposite direction. The component 20' with the drum 166 is now located above the receiving element 12. In this position a test strip can be pushed out of the drum 166 which takes up the sample volume by means of a capillary and transports it to a test field. The measuring optics located below the drum can then carry out the measurement. Subsequently the used test strips are pulled back into the drum for disposal.

This allows a complete integration of the following operating steps in a single instrument:

automatic blood collection
automatic blood application onto a test carrier
storage of unused test carriers
disposal of used test carriers.

The handling is considerably simplified for the user and the entire measurement process can take place in a substantially automated manner.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modification and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. An analytical instrument for assaying body fluids, comprising:
   a housing provided with a receiving element for engaging a body part;
   an abutment for contacting the body part, wherein the abutment can be brought into a release position and an operating position relative to the receiving element;
   a lancing unit having a lancing element that can pierce the body part, the lancing unit including a lancet drive;
   a test tape unit having a test tape for receiving body fluid issuing from the body part; and
   a detecting unit for examining the body fluid applied to a section of the test tape;
   wherein the lancing unit and the tape unit are movable alternately to and from the operating position as a common assembly relative to the housing;
   wherein the abutment is movable to the operating position to contact the body part before the lancing element initiates a lancing stroke.

2. The analytical instrument of claim 1, wherein the section of test tape to be loaded with body fluid can be transported into the area of the receiving element in the release position of the abutment.

3. The analytical instrument of claim 1, wherein the lancing unit and the test tape unit can be alternately brought into a functional position relative to the receiving element by utilizing a positioning device.

4. The analytical instrument of claim 1, wherein the abutment is formed by a front surface of the lancing unit which faces the receiving element in the operating position.

5. The analytical instrument of claim 1, wherein the lancing unit and the test tape unit are mounted on a common support.

6. The analytical instrument of claim 5, wherein the assembly can be moved on a curved path.

7. The analytical instrument of claim 5, wherein the assembly can be moved linearly in a linear guide.

8. The analytical instrument of claim 1, wherein a linkage is arranged between the housing and a common support structure for the lancing unit and test tape unit.

9. The analytical instrument of claim 1, wherein the abutment can be moved to a limited extent in the lancing direction by a curve control device.

10. The analytical instrument of claim 1, wherein the test tape unit forms a tape loop in the area of the receiving element.

11. The analytical instrument of claim 1, wherein the abutment in the operating position forms a reference means for determining the magnitude of the lancing stroke.

12. The analytical instrument of claim 1, wherein the abutment or the test tape is provided with a piercing opening for the lancing element.

13. The analytical instrument of claim 1, wherein the lancing unit has a trigger for manually actuating the lancing stroke.

14. The analytical instrument of claim 1, wherein the test tape unit comprises a tape cassette for transporting the test tape in sections.

15. The analytical instrument of claim 1, wherein a plurality of lancets is stored in a lancet magazine of the lancing unit.

16. The analytical instrument of claim 1, wherein the test tape has at least 15 sections of test tape that can be positioned relative to the receiving element by advancing the tape for successive examinations of body fluid.

17. The analytical instrument of claim 16, wherein a plurality of lancets are stored in a lancet magazine of the lancing unit and the ratio of stored lancing elements to test tape sections is between 1:1 and 1:50.

18. The analytical instrument of claim 1, wherein the receiving element has a compression element for increasing the internal pressure of the body fluid in the pressed body part.

19. The analytical instrument of claim 18, wherein the compression element comprises a conical press ring for bulging the body part against the lancing element.

20. The analytical instrument of claim 1, wherein the lancing unit or the test tape unit has a distal head member which tapers towards the receiving element.

21. The analytical instrument of claim 1, wherein the abutment can be moved into the release position and the operating position by a displacement or compression movement of the receiving element.

22. The analytical instrument of claim 1, wherein the detection unit is aligned with several measuring points located next to one another on one section of the test tape in order to check the dose of the applied body fluid.

23. The analytical instrument of claim 1, wherein the abutment is movable to the operating position in which the abutment contacts the body part before the lancing element initiates a lancing stroke.

24. The analytical instrument of claim 1, wherein the abutment and lancing element are moved together to the release position.

25. The analytical device of claim 1, further comprising an adjusting device for adjusting the lancing stroke relative to the abutment.

26. An analytical device for assaying body fluids, comprising:
   a housing having a receiving element for engaging a body part;
   a lancing unit having a lancing element for piercing the body part;
   an abutment for contacting the body part, the abutment being movable between a release position and an operating position relative to the receiving element and being movable to the operating position in which the abutment contacts the body part before the lancing element initiates a lancing stroke;
   a test tape unit having a test tape for receiving body fluid emerging from the body part; and
   a detecting unit for analyzing the body fluid applied to a section of the test tape;
   wherein the lancing unit and test tape unit can be moved alternately into the area of the receiving element on separate paths by separate delivery drives that are mechanically coupled to one another through shared gearing.

27. The analytical device of claim 26, wherein, when the abutment is in the release position, the section of test tape for receiving the body fluid is transported into the area of the receiving element.

28. The analytical device of claim 26, wherein the delivery drives comprise a common gear.

29. The analytical device of claim 26, wherein the abutment is formed by a front surface of the lancing unit which faces the receiving element in the operating position.

30. The analytical device of claim 26, wherein, in the operating position, the abutment forms a reference position for determining a magnitude of a lancing stroke.

31. The analytical device of claim 26, wherein, in the release position, a free space is defined between the abutment and receiving element for the test tape to receive the body fluid.

32. The analytical device of claim 26, further comprising an adjusting device for adjusting the lancing stroke relative to the abutment.

33. The analytical instrument of claim 26, wherein the delivery drives comprise a rack-and-pinion drive or rotary lever drive.

34. An analytical instrument for assaying body fluids comprising:
   a housing provided with a receiving element for engaging a body part;
   an abutment for contacting the body part and the abutment can be brought into a release position and an operating position relative to the receiving element;
   a lancing unit having a lancing element that can pierce the body part;
   a test tape unit having a test tape for receiving body fluid issuing from the body part; and
   a detecting unit for examining the body fluid applied to a section of the test tape;
   wherein the test tape unit has a reciprocating deflecting head that is movable from the test tape unit toward the receiving element to pull a tape loop from the test tape unit and to transport the tape loop to the receiving element.

35. The analytical instrument of claim 34, wherein the tape loop is movable to the site of blood collection.

36. The analytical instrument of claim 34, wherein the tape loop comprises a roller which executes a swivel movement.

37. An analytical device for assaying body fluids, comprising:
   a housing having a receiving element for engaging a body part;
   a lancing unit having a lancing element for piercing the body part;

an abutment for contacting the body part, the abutment being movable between a release position and an operating position relative to the receiving element and being movable to the operating position in which the abutment contacts the body part before the lancing element initiates a lancing stroke;
a test tape unit having a test tape for receiving body fluid emerging from the body part; and
a detecting unit for analyzing the body fluid applied to a section of the test tape;
wherein the lancing unit and test tape unit can be moved alternately into the area of the receiving element on separate paths by separate delivery drives that are mechanically coupled to one another, wherein movement of the lancing unit to the operating position occurs simultaneously with movement of the test tape unit.

38. The analytical device of claim 37, wherein, when the abutment is in the release position, the section of test tape for receiving the body fluid is transported into the area of the receiving element.

39. The analytical device of claim 37, wherein the delivery drives comprise a common gear.

40. The analytical device of claim 37, wherein the abutment is formed by a front surface of the lancing unit which faces the receiving element in the operating position.

41. The analytical device of claim 37, wherein, in the operating position, the abutment forms a reference position for determining a magnitude of a lancing stroke.

42. The analytical device of claim 37, wherein, in the release position, a free space is defined between the abutment and receiving element for the test tape to receive the body fluid.

43. The analytical device of claim 37, further comprising an adjusting device for adjusting the lancing stroke relative to the abutment.

44. The analytical instrument of claim 34, wherein the deflecting head is tapered in a convex or angled manner towards the receiving element.

45. The analytical instrument of claim 34, wherein the detection unit is located in the deflecting head.

46. The analytical instrument of claim 34, wherein the deflecting head pulls out the loop of the test tape in the area of the receiving element.

47. The analytical instrument of claim 46, wherein the deflecting head comprises a spring elastic deflection tongue which guides the test tape.

48. The analytical instrument of claim 46, wherein the tape deflecting head comprises a reciprocating deflecting roller which guides the test tape.

49. The analytical instrument of claim 46, wherein the deflecting head comprises a reciprocating drive for pulling out and retracting the tape loop.

* * * * *